(12) United States Patent  
Stevens et al.

(10) Patent No.: US 8,253,115 B1
(45) Date of Patent: Aug. 28, 2012

(54) INFRARED FLUORESCING OPTICAL SIGNATURE AGENT FOR REAL TIME CHANGE DETECTION

(75) Inventors: Mark A. Stevens, Oviedo, FL (US); Leslie D. Kramer, Longwood, FL (US); Randy Pike, Grant, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 821 days.

(21) Appl. No.: 11/561,716

(22) Filed: Nov. 20, 2006
(Under 37 CFR 1.47)

Related U.S. Application Data

(60) Provisional application No. 60/739,880, filed on Nov. 22, 2005.

(51) Int. Cl.
*F21K 2/00* (2006.01)
(52) U.S. Cl. ..................................... 250/458.1
(58) Field of Classification Search ..... 250/458.1–461.1
See application file for complete search history.

(56) References Cited

U.S. PATENT DOCUMENTS

| | | | |
|---|---|---|---|
| 3,899,213 A | 8/1975 | Fantasia et al. | |
| 4,329,393 A * | 5/1982 | LaPerre et al. | 428/325 |
| 4,651,010 A | 3/1987 | Javan | |
| 5,972,638 A | 10/1999 | Burlage et al. | |
| 6,025,200 A * | 2/2000 | Kaish et al. | 436/56 |
| 6,577,657 B1 * | 6/2003 | Elschner et al. | 372/39 |
| 7,336,351 B1 | 2/2008 | Sweatt et al. | |
| 7,488,954 B2 * | 2/2009 | Ross et al. | 250/458.1 |
| 2003/0021998 A1 * | 1/2003 | Hubbard et al. | 428/412 |
| 2003/0072004 A1 | 4/2003 | Huang | |
| 2003/0113540 A1 * | 6/2003 | Anderson et al. | 428/403 |
| 2004/0031931 A1 * | 2/2004 | Mu ller et al. | 250/458.1 |
| 2004/0261655 A1 * | 12/2004 | Newbacher et al. | 106/31.01 |
| 2005/0017079 A1 | 1/2005 | Psaltis et al. | |
| 2005/0095715 A1 * | 5/2005 | Hubbard et al. | 436/56 |
| 2005/0110978 A1 | 5/2005 | Potyrailo et al. | |
| 2006/0118741 A1 * | 6/2006 | Ross et al. | 250/556 |
| 2007/0102635 A1 * | 5/2007 | Ma et al. | 250/338.1 |

* cited by examiner

*Primary Examiner* — David Porta
*Assistant Examiner* — Casey Bryant
(74) *Attorney, Agent, or Firm* — Jeffrey D. Myers; Samantha A. Updegraff; Vernon Williams

(57) ABSTRACT

A method of detecting changes in a scene comprising placing a fluorescent and/or phosphorescent compound in the scene and monitoring for elimination or change in position of the phosphorescent compound. Also a liquid fluorescent and/or phosphorescent material comprising one or more compounds that are fluorescent and/or phosphorescent in infrared frequencies and substantially not fluorescent and/or phosphorescent in visible light frequencies and a carrier.

7 Claims, No Drawings

INFRARED FLUORESCING OPTICAL SIGNATURE AGENT FOR REAL TIME CHANGE DETECTION

CROSS-REFERENCE TO RELATED APPLICATIONS

This application claims priority to and the benefit of the filing of U.S. Provisional Patent Application Ser. No. 60/739,880, entitled "Infrared Fluorescing Optical Signature Agent for Real Time Change Detection", filed on Nov. 22, 2005, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to unobtrusive methods and apparatuses for detecting changes in a scene.

2. Description of Related Art

Security, surveillance, and defense systems use imaging sensors to monitor unattended areas for evidence of unauthorized access, theft, tampering, and placement of bombs or other undesirable devices. It is most desirable to have such a surveillance system be capable of identifying threats without man-in-the-loop monitoring.

Current systems to detect changes in imagery employ storage of the previous images. The new data is then compared to the stored data using an intensive processing system. The two sets of imagery are digitized, and loaded into memory. Multiple frames are stitched together into a super-frame of data. The algorithm then looks for recognizable features in the scenery. These features are used as anchor points to register the two sets of data properly so as to reduce the rate of false alarms. Then, each pixel is subtracted from the corresponding, re-registered pixel in the older data set.

The present invention is of a material and method of use that drastically reduces the amount of computation needed to determine scene changes. One application for the present invention is in the monitoring of roadside guardrails and debris piles in Iraq, where Improvised Explosive Devices (IEDs) are being placed. A second potential use for the material of the invention is as an optical marker tag on vehicles suspected of containing car-bombs. Classical architectures for this require extensive processing power and time to reduce the data. The effectiveness of these systems will be greatly enhanced by the ability to identify specific areas of the imagery where something has changed recently.

BRIEF SUMMARY OF THE INVENTION

The present invention is of a method of detecting changes in a scene, comprising: placing a fluorescent and/or phosphorescent compound in the scene; and monitoring for elimination or change in position of the phosphorescent compound. In the preferred embodiment, placing comprises placing a compound that is fluorescent and/or phosphorescent in infrared frequencies, preferably one that is substantially not fluorescent or phosphorescent in visible light frequencies. The monitoring step can occur by aircraft or satellite, and the scene can be illuminated with laser light. Preferred inorganic compounds are erbium-doped InGaN, GaN/ZnSe, AlGaAs, AlGaN, silica nanoparticles with zinc nanocores, and zinc sulfide. Preferred organic compounds are 4-(Dicyanomethylene)-2-methyl-6-(4-dimethylaminostyryl)-4H-pyran, 5,12-Dihydro-5,12-dimethylquino[2,3-b]acridine-7,14-dione, Coumarin derivatives, poly(1-vinylnaphthalene, poly(2-vinylnaphthalene, and polyaniline. One can additionally place an organic binding receptor material.

The invention is also of a liquid fluorescent and/or phosphorescent material comprising: one or more compounds that are fluorescent and/or phosphorescent in infrared frequencies and substantially not fluorescent and/or phosphorescent in visible light frequencies; and a carrier. Preferred inorganic compounds are erbium-doped InGaN, GaN/ZnSe, AlGaAs, AlGaN, silica nanoparticles with zinc nanocores, and zinc sulfide. Preferred organic compounds are 4-(Dicyanomethylene)-2-methyl-6-(4-dimethylaminostyryl)-4H-pyran, 5,12-Dihydro-5,12-dimethylquino[2,3-b]acridine-7,14-dione, Coumarin derivatives, poly(1-vinylnaphthalene, poly(2-vinylnaphthalene, and polyaniline. An organic binding receptor material can be included, preferably comprising one or more of activated telomerase polymers, biological entities, and bio-functionalized emissive infrared bandgap compounds, most preferably including poly(phenylene vinylene). The carrier preferably comprises water and a carrier material, most preferably ethyl alcohol, methyl alcohol, isopropyl alcohol, ammonia, or alkyl dispersants.

Objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

Not Applicable.

DETAILED DESCRIPTION OF THE INVENTION

The Optical Signature Agent of the present invention is preferably a viscous coating that can be sprayed over an area to be monitored. The agent preferably comprises an infrared fluorescing polymer material in a low-cost carrier such as SolGel. The agent preferably has a unique optical phosphorluminescence, with a strong signature that can be observed by the camera or sensor system. The material will absorb optical energy, either solar or from an illuminator device, and re-emit this energy with the specified signature. The signature can be multi-spectral, or hyperspectral if required for anti-spoofing reasons.

Since the agent is deployed over a large area, the emission will be relatively uniform throughout the region being monitored. Any articles introduced into the area, items moved, or removed since the agent was broadcast will immediately be apparent in the imagery. In the example of the IEDs in Iraq, the optical agent can be sprayed from a helicopter in cleared areas. Periodic flights over this area with the IR imaging system, tuned to match the spectral signature of the agent will immediately identify areas where new items have been introduced or items have been moved. One such imaging system being developed by the Army is the Lightweight Airborne Minefield Detection System (LAMD). This system also employs a wide field Infrared Laser which could energize the optical agent for night flights. The LAMD system incorporates geo-location hardware to pinpoint the anomalies. Surveillance of a car-bomb will be considerably facilitated when the suspected vehicle radiates light that can be seen from a Police helicopter.

The broad area Optical Signature Agent is a passive application that does not require any type of data storage or processing hardware to perform image subtraction. Real time display of analog imagery will plainly show discontinuities in the spectral signature anywhere there has been a change in the scene since the last application of the agent. A comprehensive monitoring system, such as one comprising a central server or computer cluster, can identify the location of these anomalies as the camera is swept over the scenery, and report these locations to monitoring personnel or automated systems for further interrogation.

The preferred Optical Signature Agent preferably comprises an environmentally friendly paint with a phosphorescent compound similar to plastic children's toys that glow in the dark. However, the agent is preferably clear and emits light in the infrared, making it invisible to the human eye. This compound is used in concert with an infrared surveillance camera system that can track any object that has been marked with the agent, or detect any previously sprayed areas where something has been disturbed.

To reiterate, Improvised Explosive Devices (IEDs) are becoming an ubiquitous problem. Note the following points regarding ways in which to locate them: (1) An automated target recognition algorithm is unlikely to work, since the devices are homemade and all look different; (2) Most imaging sensor systems will not pick up IEDs, as they are often concealed; (3) Chemical sensors may work well if they are directed to a specific location to interrogate; (4) A sensor that detects changes in the image can point out locations where something has been introduced, moved, or removed; (5) Classical surveillance sensors can only detect change via an extensive digital image storage and processing technique, which is prone to a high false alarm rate, and requires considerable time to complete; (6) What is required is a technique of detecting a change in the area of interest in real time, without the need to perform sophisticated processing; and (7) Cleared and secured roadways, for example, can be sprayed with the Optical Signature Agent of the invention—then an airborne sensor can be flown ahead of troop movements and search for anomalies, which can then be interrogated or avoided.

The preferred agent of the invention has a unique optical phosphor-luminescence, with a strong signature that can be observed by the camera, or sensor system. The material absorbs optical energy, either solar or from an illuminator device, and re-emits this energy with the specified signature. The signature can be multi-spectral, or hyper-spectral if required for anti-spoofing reasons. Since the agent is deployed over a large area, the emission will be relatively uniform through out the region being monitored. Any articles introduced into the area, items moved, or removed since the agent was broadcast will immediately be apparent in the imagery. An airborne sensor can radio coordinates of detected anomalies to following troops. An airborne laser illuminator can be employed to ensure that the agent will have energy to emit, even at night.

The compounds of the invention preferably exhibit the following properties, or at least a subset thereof: (1) Infrared (IR) emitters (radiative transition); (2) Fluorescence (strong—vib.) and/or phosphorescence (weak—vib.); (3) Low bulk cost; (4) Non-toxic liquid dispersive; (5) Aerosol (air compressive)–nitrogen carriers; (6) Bulk mass>air; and (7) Sensitivity for selective binding with IED compounds containing one or more of —$NO_2$, —$NH_3$, —$ClO_4$, —$MnO_4$, or —$NO_3$ linkages.

Potential low cost and environmentally friendly carrier systems for dispersing IR emitting compounds include: (1) Ethyl Alcohol/Aqueous–(10-50% EA)/(90-50% $H_2O$); (2) Methyl Alcohol/Aqueous–(10-50% MA)/(90-50% $H_2O$); (3) Isopropyl Alcohol/Aqueous–(10-50% IA)/(90-50% $H_2O$); (4) Ammonia/Aqueous–(10-20% $NH_3$)/(90-80% $H_2O$); and (5) Aqueous+alkyl ($Na^+$, $Mg^{2+}$, $K^+$) dispersant.

The preferred IR emitting compounds emit in approximately the 2.5-4.5 micron bandgap. Preferred emissive compounds specifically include both inorganic and organic compounds. Inorganic compounds include: (1) InGaN/Erbium Doped; (2) GaN/ZnSe; (3) AlGaAs; (4) AlGaN; (5) Silica Nanoparticles/Zinc Nanocores; and (6) Zinc Sulfide. Organic Compounds include (which can have primary fluorescence in the visible region): (1) DCM (4-(Dicyanomethylene)-2-methyl-6-(4-dimethylaminostyryl)-4H-pyran) dye (Sigma-Aldrich product 41,049-7); (2) Especially when used as the emissive dopant in an Alq (tris(8-quinolinolato) aluminum) host layer, DMQA (5,12-Dihydro-5,12-dimethylquino[2,3-b]acridine-7,14-dione) (Sigma-Aldrich product 55,758-7) provides improved operational stability; (3) Coumarin derivatives, which have been employed as dopants in PVK (polyvinyl carbazole) based multilayered EL (electroluminescent) devices; (4) Poly(1-vinylnaphthalene) (Sigma-Aldrich product 19,193-0); (5) Poly(2-vinylnaphthalene) (Sigma-Aldrich product 46,194-6); and (6) Polyaniline.

The preferred Organic Binding Receptor Materials (COTS) for attachment to high explosive compounds include: (1) Activated telomerase polymers (ATP), such as Poly(phenylene vinylene) backbone polymerics; (2) Potential biological entities; and (3) Bio-functionalized emissive IR bandgap compounds.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A liquid fluorescent and/or phosphorescent material comprising:
    one or more compounds that are fluorescent and/or phosphorescent in infrared frequencies and substantially not fluorescent and/or phosphorescent in visible light frequencies;
    said one or more compounds comprising an inorganic compound and an organic compound;
    an organic binding receptor material; and
    a carrier;
    an aerosol sprayable from an airborne vehicle; and
    an emission in approximately the 2.5 to 4.5 micron bandgap.

2. The material of claim 1 wherein said one or more compounds comprise an inorganic compound selected from the group consisting of erbium-doped InGaN, GaN/ZnSe, AlGaAs, AlGaN, silica nanoparticles with zinc nanocores, and zinc sulfide.

3. The material of claim 1 wherein said one or more compounds comprise an organic compound selected from the group consisting of 4-(Dicyanomethylene)-2-methyl-6-(4-dimethylaminostyryl)-4H-pyran, 5,12-Dihydro-5,12-dimethylquino[2,3-b]acridine-7,14-dione, Coumarin derivatives, poly(1-vinylnaphthalene, poly(2-vinylnaphthalene, and polyaniline.

4. The material of claim 1 wherein said organic binding receptor material comprising one or more of the group consisting of activated telomerase polymers, biological entities, and bio-functionalized emissive infrared bandgap compounds.

5. The material of claim 4 wherein said organic binding receptor material comprises poly(phenylene vinylene).

6. The material of claim 1 wherein said carrier comprises water and a carrier material.

7. The material of claim 6 wherein said carrier material comprises a material from the group consisting of ethyl alcohol, methyl alcohol, isopropyl alcohol, ammonia, and alkyl dispersants.

* * * * *